(12) United States Patent
Trachtenberg et al.

(10) Patent No.: US 8,548,562 B2
(45) Date of Patent: Oct. 1, 2013

(54) SYSTEM AND METHOD OF GUIDED TREATMENT WITHIN MALIGNANT PROSTATE TISSUE

(76) Inventors: John Trachtenberg, Toronto (CA); Masoom A. Haider, Richmond Hill (CA); Brian Campbell Wilson, Toronto (CA)

( * ) Notice: Subject to any disclaimer, the term of this patent is extended or adjusted under 35 U.S.C. 154(b) by 1454 days.

(21) Appl. No.: 11/724,750

(22) Filed: Mar. 16, 2007

(65) Prior Publication Data

US 2007/0230757 A1   Oct. 4, 2007

Related U.S. Application Data

(60) Provisional application No. 60/788,954, filed on Apr. 4, 2006.

(51) Int. Cl.
*A61B 5/05* (2006.01)

(52) U.S. Cl.
USPC ........... 600/411; 600/407; 600/420; 600/427; 600/439; 600/471; 601/2; 601/3; 606/11; 606/12; 606/27; 607/61; 607/62; 607/96; 607/100; 604/19; 604/20

(58) Field of Classification Search
USPC ................. 600/407, 411, 420, 427, 439, 471; 601/2, 3; 606/11, 12, 27; 607/61, 62, 96, 607/100; 604/19, 20
See application file for complete search history.

(56) References Cited

U.S. PATENT DOCUMENTS

| | | | |
|---|---|---|---|
| 5,491,627 A | 2/1996 | Zhang et al. | 600/408 |
| 5,588,435 A | 12/1996 | Weng et al. | 600/443 |
| 6,058,322 A * | 5/2000 | Nishikawa et al. | 600/408 |
| 6,504,959 B1 | 1/2003 | Lee | 382/260 |
| 6,575,969 B1 | 6/2003 | Rittman, III et al. | 606/41 |
| 6,618,620 B1 * | 9/2003 | Freundlich et al. | 607/27 |
| 2002/0026127 A1 * | 2/2002 | Balbierz et al. | 600/567 |
| 2004/0214204 A1 * | 10/2004 | Ross | 435/6 |
| 2005/0014710 A1 | 1/2005 | Sun et al. | 514/44 |
| 2005/0113651 A1 * | 5/2005 | Wood et al. | 600/300 |
| 2006/0104902 A1 * | 5/2006 | Powis et al. | 424/9.1 |

\* cited by examiner

*Primary Examiner* — Unsu Jung
*Assistant Examiner* — Joseph M Santos Rodriguez
(74) *Attorney, Agent, or Firm* — Mark A. Litman & Associates, P.A (57) ABSTRACT

An imaging and diagnostic system and method to differentiate between malignant and non-malignant tissue of a prostate and surrounding region. The system acquires imaging data from the prostate and surrounding proximal region, and processes the data to differentiate areas of tissue malignancy from non-malignant tissue. A sectioning device or ablative device is provided. The ablative device is operable by automation for receiving the imaging output coordinates and defining the trajectory and quantity of energy or power to be delivered into the malignant tissue. A control system determines calculated energy or power to be deposited into the malignant tissue during ablation, to minimize destruction of the non-malignant tissue within the prostate and surrounding tissue. The system operates on generated ablative device output data.

16 Claims, 3 Drawing Sheets

IMAGING SYSTEM THAT PROVIDES DIGITAL DATA (e.g., MAGNETIC RESONANCE IMAGING SYSTEM)

↓

TRANSMISSION OF DIGITAL DATA TO PROCESSOR WITH EVALUATIVE SOFTWARE

↓

MONITOR DISPLAYING IMAGING DIGITAL DATA

↓

EVALUATION OF DIGITAL DATA TO DETERMINE SIZE, SHAPE AND ORIENTATION OF STATISTICAL POTENTIAL FOR MALIGNANCY

↓

GENERATION OF PLANNING STRATEGY IN PROCESSOR

↓

SURGICAL INSTRUMENTATION

↓

DIRECTION AND IMPLEMENTATION OF PLAN FROM PROCESSOR

FIG. 1

IMAGING SYSTEM THAT PROVIDES DIGITAL DATA (e.g., MAGNETIC RESONANCE IMAGING SYSTEM)

↓

TRANSMISSION OF DIGITAL DATA TO PROCESSOR WITH EVALUATIVE SOFTWARE

↓

MONITOR DISPLAYING IMAGING DIGITAL DATA

↓

EVALUATION OF DIGITAL DATA TO DETERMINE SIZE, SHAPE AND ORIENTATION OF STATISTICAL POTENTIAL FOR MALIGNANCY

↓

GENERATION OF PLANNING STRATEGY IN PROCESSOR

↓

SURGICAL INSTRUMENTATION

↓

DIRECTION AND IMPLEMENTATION OF PLAN FROM PROCESSOR

SYSTEM AND METHOD OF GUIDED TREATMENT WITHIN MALIGNANT PROSTATE TISSUE

RELATED APPLICATION DATA

This application claims priority from U.S. Provisional Patent Application No. 60/788,954 filed Apr. 4, 2006.

BACKGROUND OF THE INVENTION

1. Field of the Invention

The invention relates to systems and method of planning treatments, execution of treatments and imaging. By using imaging techniques and data to differentiate between malignant and non-malignant prostate tissue, tissue removal such as by means of sectioning and ablation is directed to the malignant tissue, for preservation of the non-malignant tissue in the prostate and surrounding region, thereby minimizing the destructive effects of tissue removal.

2. Background of the Art

Prostate cancer is widely believed to be the most common cancer in men and the second most common cause of death due to cancer. There were approximately 230,000 reported cases of prostate cancer diagnosed in North America in 2005 and over 30,000 deaths. Furthermore, the true prevalence of the disease has been calculated at more than 25% of men over 55. The standard treatments for localized prostate cancer are radical surgery or radiotherapy. These entail ablation of the entire prostate with some degree of unintended collateral damage to surrounding organs. The standard belief is that prostate cancer is a multifocal disease so that treatments are required that target the entire prostate gland. These treatments are neither completely curative nor devoid of side effects. Recent data suggest that this may not be correct in all cases. For the majority of patients low grade and low volume prostate cancer is the prevalent pathological finding and offers minimal risk of morbidity or mortality. Indeed, many believe that radical intervention using standard treatments might offer more harm than good and a strategy of deferred treatment is now being adopted. However, even in this favorable group approximately 20% of men can be expected to die from their disease if followed for long enough.

A new paradigm of therapy is to target selective therapeutic destruction of only the region of malignant (tumor) tissue within the prostate. A histological analysis of over 900 prostatectomy specimens removed for prostate cancer suggest that a solitary dominant lesion is the source of extracapsular in over 80% of patients and thus the likely source of extra-prostatic spread. Destruction of this single site is likely to significantly decrease the risk of progression and increase cancer control with minimal side effects.

SUMMARY OF THE INVENTION

A system and method to identify the malignant tissue region and a method to focally and selectively destroy the tumor tissue is disclosed for the diagnosis of malignant tissue and prevention of unnecessary damage to non-malignant tissue in the delivery of ablation. The enabled technology is achieved through convergence of technologies that include accurate imaging to detect and target the malignant tissue within the prostate, an appropriate tissue removal systems such as automated (e.g., robotic) sectioning devices or an ablative device and energy source or any other appropriate surgical device, guided delivery of activity in the automated device or energy from the ablative device, the use of software being optional but preferred in planning, manipulation, and imaging following ablation such that only the target malignant is destroyed as may be confirmed by subsequent imaging of the target. The components may be employed sequentially over short or long time span. Advantages of the invention may include at least some of the following: a) improved accuracy in imaging and localization of the tumor (malignant tissues) within the prostate is a result of a novel magnetic resonance imaging-based technique or other contrast-enhancing imaging modalities; b) improved planning for optimizing delivery of therapy to the focal malignant tissue with minimal damage outside the focal volume, based on pre-treatment imaging with or without biopsy; c) improved delivery of ablative therapy to the malignant tissue, such ablative therapy comprising any of thermal therapy (using laser, ultrasound, radiofrequency or microwave energy sources); photodynamic therapy (using a combination of a photosensitizing drug and an activating light source); radiation treatment using either implanted radioactive sources or external ionizing radiation beams; mechanical or other surgical devices to perform a partial prostatectomy; local injection of an anti-cancer agent (drug, biologic, gene, noxious agent);

a) improved safety of the system and method through use of minimally-invasively delivery of treatment based on the planning, with or without on-line sensing and/or imaging of the treatment delivery and tissue response; and b) assessment of the effectiveness of destruction of the target malignant tumor tissue.

In one aspect of the technology described herein, aspects of the present invention provide an imaging system for differentiating between malignant and non-malignant tissues within the prostate region and for guided delivery of specific focal ablation or surgical resection tool to and within the malignant tissues of the prostate, and away from the non-malignant tissues, the system comprising:

a) at least one imaging device for receiving image data, processing imaging data and outputting information (which may be in various informative content such as image data or graphic location data, coordinates, perspectives, and the like) bearing on or indicating the size, location and orientation of the malignant tissue;

b) a surgical system (e.g., an energy source and an ablative device for removing tissue such as cutting devices, sectioning devices, ablative devices for deposition of energy into the malignant prostate tissue; and means for quantifying a surgical procedure (such as the energy delivered from the ablative device into the tissue, mass of tissue removed, etc.);

wherein the surgical procedure (e.g., ablative energy) is focally delivered by the (e.g.,) ablative device to the malignant tissue under image surveillance so as to substantially avoid destruction of the non-malignant tissue of the prostate.

In another aspect of the technology described herein, the present invention also includes a method of using an ablative device to deliver energy to a malignant prostate region, comprising the steps of: a) differentiating malignant and non-malignant tissues of a prostate, as by identifying the size, location and orientation of the malignant tissue using an imaging device providing an image display; b) calculating the size, location and orientation of the malignant and non-malignant tissue of the prostate represented on the image display; c) providing an energy source through or from an ablative device to deliver focal ablation to the malignant tissue of the prostate; d) operating a monitoring system arranged to quantify the amount of energy deposited by the ablative device, representative of physiological changes caused by the ablation and to generate output data; and e) delivering focal therapeutic treatment to the malignant tissue of the prostate, in an amount being responsive to the output data of the monitoring system.

According to a further aspect of the technology described herein, the invention includes a method of using a surgical device to resect malignant tissue of a prostate, comprising the steps of: a) differentiating malignant and non-malignant tissues of a prostate, as by identifying the size, location and orientation of the malignant tissue using an imaging device providing an image display; b) calculating the size, location and/or orientation of the malignant and non-malignant tissue of the prostate represented on the image display; and c) providing a surgical device to remove the malignant tissue of the prostate.

According to another aspect of the invention described herein, the invention includes a method of operating a monitoring system to display the remaining prostate tissue during or after surgical removal of the malignant tissue to ensure complete removal of the malignant tissue.

According to another aspect of the invention described herein, the invention includes a computer implemented method for identifying and localizing malignant tissues of a prostate, using T2 weighted imaging, dynamic contrast enhanced imaging, and, diffusion-weighted imaging, comprising the steps of:
  a) generating a series of axial images through the prostate;
  b) inputting variable "a" to represent the presence of malignant tissue and variable "b" to represent the absence of malignant tissue in accordance with T2 weighted, diffusion weighted, and dynamic contrast enhanced images, acquired spanning the prostate tissue;
  c) using a T1 weighted pulse sequence to obtain at least one dynamic contrast enhanced image;
  d) generating an apparent diffusion coefficient map (ADC) on an MRI scanner using standard software;
  e) administering an intravenous contrast agent;
  f) generating a map of parameters from the dynamic contrast enhanced images using a pharmacokinetic model; and
  g) automatically generating a value reflecting the likelihood of cancer by weighting pre-determined regions of the prostate using a combination of the T2, ADC, and dynamic contrast enhanced parameter maps, This technique may be further enhanced with the use of MR spectroscopy, quantitative T2 mapping or T2* mapping pulse sequences on the MRI system
  h) Color code and process the image to optimally display the tumor on the background normal prostate
to determine the size, location, and orientation of the malignant and non-malignant tissue of the prostate represented on the image display.

According to another aspect of the invention described here, the invention includes an imaging system for differentiating between malignant and non-malignant tissues within the prostate region and for guided delivery of surgical resection to and within the malignant tissues, the system comprising:
  a) at least one imaging device for receiving, processing and outputting the size, location and orientation of the malignant tissue;
  b) a surgical device placed into the prostate, either by the operator based on the display of the target malignant tissue in the prostate from the imaging device or by attaching the surgical device to a positioning device capable of receiving data from the imaging device,
and c) translating these data into spatial coordinates that define the position of the surgical device with respect to the position of the target malignant tissue.

DETAILED DESCRIPTION OF THE PREFERRED EMBODIMENT

The technology described herein relates generally to apparatus, systems and methods for the treatment of cancer by removal of cancerous (malignant) tissue and cells, while attempting to minimize the removal of or damage to benign (non-cancerous) cells and tissue. The technology described herein is particularly useful for the treatment of prostate cancer where visualization of the tumors, cancerous tissue and differentiation from benign tissue has proven to be difficult by other means. The technology includes, by way of a non-limiting description, at least one imaging system (particularly an imaging system that directly provides digital image information or an analog imaging system having a processor that can convert analog imaging data into digital data) that provides data for differentiating between malignant and non-malignant tissues, especially within the prostate region of a patient. The system may also enable guided (automated, robotic, processor plan directed) delivery of tissue removal instrumentation (both for ablative and/or surgical sectioning techniques, by manual or computer-guided formats) to and within the malignant tissues of the prostate, and away from the non-malignant tissues. A general description of a useful system may include, again by way of non-limiting examples, a) at least one imaging device for providing imaging data. The system may use analog or digital imaging capture, but ultimate provision as digital data for automated review is preferred. A processor is provided to receive the imaging data and execute software to evaluate the image data according to at least one algorithm. One function that may be provided by the software is to evaluate imaging data according to predetermined standards that are considered in the medical field to be indicative of the appearance of malignant tissue in the region of examination, such as the prostate. The software may be self-executing (e.g., it automatically reads and interprets data, or may pseudo-self-executing with a user inputting partial information to the processor where it is felt that the software should be executed with respect to data in regions and conditions identified by the user input partial information. For example, the processor operator may virtual circle or highlight regions on a view of the imaged field to accentuate regions which to the operators perceptions should be computer evaluated in greatest detail. For example, the imaging information, especially where digitized or initially digital, is provided as columns and rows of imaging data (e.g., pixels or bits in columns and rows of the entire image. By using a touchscreen display of regions of image to the user, regions within the image may be circumscribed, highlighted, detailed, identified or input into the processor as segments of the total image data that can should be particularly screened, analyzed, reviewed, or examined by execution of the software on imaging data within the area of the touchscreen (or other image area selection, as by mouse, coordinate input from an image with an overlaid matrix) identified as of particular interest.

The software may use various analytical techniques that use inclusive, exclusive, edge features, density variations, absolute densities, thermal variations, shape identification and the like to assist in the identification of suspect tissue. The analysis may be on a scholastic basis, assigning relatively subjective values to imaging data that is indicative of a level of probability for tissue to be malignant because of parameters evaluated in the software, percentage estimates for levels of probability, symbolic or color identification of regions according to assessed likelihood of malignancy and the like, as well as absolute standards such as optical density in comparison to a standardized element in an image. This can be done so that an observer may further inspect the regions to provide additional professional input, or to request additional image data from a particular region, as from a different orientation or perspective.

An algorithm may be used for the processing of the imaging data and outputting information relating to size, location and orientation of the malignant tissue and as indicated above, assigning automated estimates of priority for specific regions of the tissue with respect to malignancy or benignity. These assessments may be used to formulate operational procedures and formats, both with regard to the types of instrumentality that may be used in the ultimate surgical treatment and for estimation of the amount of tissue that is to be removed. Based on the probability information provided by analysis of the image data by the software and/or additional user input, plans may be formulated for assumed malignant tissue removal. The medical team, alone or even with patient consultation may decide on the extent of tissue removal (e.g., by physical incision and/or local destruction and/or mass removal, as by ablative, disruptive (sonic disruption, or sectioning) according to plans which may be generally characterized as minimal (e.g., including regions with tissue probabilities for malignancy above 75%); as conservative (e.g., including regions with tissue probabilities at higher levels than in the minimal approach, such as 50%), and radical (e.g., including regions with tissue probabilities at higher levels than in the conservative approach, such as 25%). Different plans may be constructed for suspect tissue removal based on these scholastic or probabilistic assessments of the tissue areas, either from the software alone, or software estimates enhanced by professional input.

The system must use instrumentality to perform the ultimate malignant tissue removal. The instrumentality may be manually operated systems, mechanically (e.g., robotic) operated devices, laser systems distally controlled through a processor or user input, sonic disruption, rf emitter, microwave emitter, chemical application and the like, preferably under visual performance through at least a display device (e.g., monitor or screen). Where there is sonic or laser disruption or destruction of the tissue, there must be an energy source for the operation of the system. A preferred system would be an ablative device for deposition of energy into the malignant prostate tissue.

The energy deposition system must include some control of the deposition of the energy such as a plan and automated or manual control for quantifying the energy delivered from the ablative device into the tissue. A processor is preferably used to provide the plan for the energy to be focally delivered by the ablative device to the malignant tissue under image surveillance so as to substantially avoid destruction of the non-malignant tissue of the prostate based upon the output information relating to size, location and orientation of the malignant tissue. The term focally delivered has the meaning of an identified target region or focus of the intent of the delivery of the operation, and may include, but is clearly not limited to a narrower meaning of focusing energy as through mirrors or lenses. The preferred system has the imaging device comprise an MRI device, although ultrasound, X-ray, fluoroscopy or other non-invasive imaging may be used. Invasive imaging such as fiber optic delivered electromagnetic radiation imaging (e.g., UV, visible or infrared imaging sources), but the non-invasive imaging is highly preferred because of its ease in providing intratissue imaging and larger areas of imaging. The other systems would be more likely used to supplement the non-invasive imaging or be used during actual sectioning or ablation of tissue. The system in that event could have the first imaging device as a system providing two distinct imaging capabilities consisting of an MRI device and further comprising at least a second imaging device other than an MRI device. The system or component for quantifying energy deposition from the ablative device may, by way of non-limiting examples, be a plan constructed by application of an algorithm to the imaging data in a computer program. The system may further comprise a minimally invasive monitoring device for monitoring delivery of the energy deposition to the malignant tissue sector, and the minimally invasive monitoring device also verifies non-destruction of the non-malignant tissue sector. The monitoring device may include a screen, display, monitor or the like.

A method of removing malignant tissue from a prostate using ablative energy according to the disclosed technology may be described as comprising at least the steps of taking imaging data by non-invasive imaging; executing a software program using the imaging data to provide an indication of differentiation between malignant and non-malignant tissues of a prostate, determining the size, location and orientation of the malignant and non-malignant tissue of the prostate represented on the image display; providing an energy source through or from an ablative device to deliver focal ablation to the malignant tissue of the prostate in accordance with the determined size, location and orientation of at least the malignant tissue; operating a monitoring system quantifying an amount of energy deposited by the ablative device; and delivering tissue removing focal therapeutic treatment to the malignant tissue of the prostate, in an amount responsive to the output data of the monitoring system. The method may include quantifying the amount of energy as representative of physiological changes to be caused by ablation and the quantified amount of energy generates output data to an ablative device. The obtained determination may preferably indicate size, location and orientation of the malignant tissue by application of an algorithm to the imaging data that characterizes likelihood of grades of data with respect to likelihood of malignancy versus benignity. An imaging device provides an image display during or after the determination. The plan may be prepared as a visual image of proposed location of procedures, a mapping of planned delivery of energy over specific tissue areas within regions identified as containing malignant tissue, by a printed plan in map or coordinate form, or in a database file of plan containing any of the above plan formats.

The technology described herein may also include a method of removing malignant tissue from a prostate using resection by non-ablative tools comprising the steps of: taking imaging data by non-invasive imaging; executing a software program using the imaging data to provide an indication of differentiation between malignant and non-malignant tissues of a prostate, determining the size, location and orientation of the malignant and non-malignant tissue of the prostate represented on the image display; providing a resectioning medical tool to deliver focal therapy of excision of tissue to the malignant tissue of the prostate in accordance with the determined size, location and orientation of at least the malignant tissue; monitoring the amount and location of tissue removed and comparing the tissue removing focal therapeutic treatment to determined size, location and orientation of the malignant tissue. This resectioning method may further comprise operating a monitoring system in real time to display remaining prostate tissue during or after surgical removal of the malignant tissue to ensure complete removal of the malignant tissue.

The technology described herein also encompasses a computer implemented method used in conjunction with the methods described above for energy directed tissue removal methods that includes identifying and localizing malignant tissues of a prostate, using a combination of T2 weighted imaging, dynamic contrast enhanced imaging and diffusion-weighted imaging, comprising the steps of:
 a) generating a series of axial images through the prostate;
 b) inputting variable "a" to represent the presence of malignant tissue and variable "b" to represent the absence of malignant tissue in accordance with T2 weighted, diffusion weighted and dynamic contrast enhanced images, acquired spanning the prostate tissue;
 c) using a T1 weighted pulse sequence to obtain at least one dynamic contrast enhanced image;
 d) generating an apparent diffusion coefficient map (ADC) on an MRI scanner using standard software;
 e) administering an intravenous contrast agent;
 f) generating a permeability map using a modified Brix pharmakinetic model; and
 g) automatically generating a value, by weighting predetermined regions of the permeability map.

This is a preferred, but not exclusive method for determining the size, location, and orientation of the malignant and non-malignant tissue of the prostate represented on the image display.

The technology described herein may also include an imaging system for differentiating between malignant and non-malignant tissues within the prostate region and for guided delivery of surgical resection to and within the malignant tissues, the system comprising: a) at least one imaging device for receiving, processing and outputting the size, location and orientation of the malignant tissue; b) a surgical device placed into the prostate, either by the operator based on the display of the target malignant tissue in the prostate from the imaging device or by attaching the surgical device to a positioning device capable of receiving data from the imaging device, and c) translating these data into spatial coordinates that define the position of the surgical device with respect to the position of the target malignant tissue, wherein the surgical device is manipulated under image surveillance so as to remove the malignant tissue while substantially avoiding destruction of the non-malignant tissue of the prostate, the surveillance being provided by a MR, ultrasound or other imaging device that co-registers a) the data from the imaging system used to localize the malignant tissues, b) the position of the surgical device and c) the position and orientation of the prostate during the surgical procedure. In one implementation, malignant cancer within the prostate is localized using a combination of MRI (magnetic resonance imaging) techniques and analysis of the imaging data from the MRI to weight the imaging data with respect to probabilities of tissue or tissue mass providing data indicative of malignancy. These may, for example, comprise the following:

To identify and localize prostate cancer, a format may be used, such as a combination of T2 weighted imaging, dynamic contrast enhanced imaging (DCE) and diffusion weighted imaging is performed: A series of axial images (e.g., full planar slices) is then generated through the prostate. Each region of the prostate is then scored (e.g., evaluated, analyzed to produce a basis of determining likelihood, probability or potential for the presence or absence of cancer. The determination might be based on scholastic ratings or other rankings with a scale available in graphic, look-up table or algorithm that is part of software executed on the processor. In addition to the specific formats and models used in the examples, other known alternative functions and newly developing systems may be used in the practice of this technology, such as but not limited to the use of one or more of T2 mapping, T2* mapping and proton spectroscopy and using other pharmokinetic models than Modified Brix. The article in Journal of Cerebral Blood Flow and Metabolism, Volume 26, No. 3, "Model selection in magnetic resonance imaging measurements of vascular systems" is incorporated herein by reference for discussion of such modeling systems.

One potential, non-limiting schema for acquiring and scoring the images is outlined below. T2 weighted, diffusion weighted and dynamic contrast enhanced images are acquired spanning the entire prostate volume, normally using a 1.5 T or greater MRI system. T2 weighted images are obtained in two non-parallel planes such as an axial slice and at least one other plane with a slice thickness of 3 mm or less and a field of view of 24 cm or less. In some circumstances an endorectal surface coil may be used to improve spatial resolution with a reduction of field of view to 12-14 cm. Dynamic contrast enhanced images are obtained by using a T1 weighted pulse sequence that allows for repeated imaging of the prostate at a temporal resolution of 100 s or less during the intravenous bolus administration of a low molecular weight MR contrast agent such as a gadolinium chelate (i.e., Gd-DTPA, or gadodiamide). Administration of the intravenous contrast agent may be done using a power injector at a rate of 2-4 ml/s for a total dose of 0.1-0.2 mmol/kg. Specific features used in identifying tumor sites are a relative decrease in T2 signal in the peripheral zone of the prostate combined with elevated permeability. Permeability is derived from a 2 compartment pharmacokinetic model and represents the transfer constant of the contrast agent from the vascular compartment to the tissue compartment.

A specific example of the MRI technology is described below.

MRI Protocol

As a non-limiting example, the following parameters are used to acquire images
 1. Equipment
 Examinations are performed on a 1.5 T MRI system using an endorectal coil
 2. Imaging Planes
 Oblique axial imaging are performed perpendicular to the rectoprostatic fascia.
 3. Pulse sequences
 a. Oblique axial FSE T2
 i. Imaging Parameters
  TR/TE 5650.0/100.4; ETL 16, BW 41.66, FOV 14, PFOV 1.00; slice thickness/gap 3/0 mm, NEX 3, matrix 256×256, phase encoding direction left to right, no phase wrap
 b. Oblique coronal FSE T2
 i. same as 3.a.1 but perpendicular plane
 c. Oblique Axial DWI
 i. Imaging Parameters TR/TE 4000/73.6 ms, BW 167 kHz; FOV 14.0 cm, PFOV 1.00, slice thickness/gap 3/0 mm; NEX 1; matrix 256×128; b-val 600 s/mm 2, phase encoding direction antero-posterior d. Multiphase contrast enhanced 3D FSPGR
   i. Contrast delivery
      injection of gadopentetate dimeglumine (MAGNEVIST®, Berlex, N.J., USA) using an automated injector system (Medrad, Pa., USA) at a rate of 4 cc/s and a dose of 0.1 mmol/kg with a 20 cc saline flush at 4 cc/s to commence at the same time as image acquistion.
   ii. Imaging Parameters
      Multiphase dynamic T1-weighted 3D gradient echo images will then be obtained over 5 minutes with a temporal resolution of 10 s.
      TE/TE 6.5/4.2 ms; FA 20; bw 31.25, FOV 14.0 cm; PFOV 1.00; slice thickness 3.0/0.0 mm; NEX 0.5; matrix 256×128, phase encoding direction antero-posterior Abbreviations: TR=repetition time (ms), TE=echo time (ms), BW=bandwidth (kHz); ETL=echo train length, PFOV=phase field of view, FA=flip angle (degrees), NEX=number of excitations, FOV=field of view (cm) FSE=fast spin echo, FSPGR=fast spoiled gradient recalled echo, DWI=diffusion weighted imaging Image Analysis Once the image data is acquired they may be analyzed using the following method T2 Weighted Images Regions of low signal in the peripheral zone are considered suspicious for cancer. This is a qualitative interpretation.

ADC Maps

From the DWI images (See paragraph c) an apparent diffusion coefficient (ADC) map can be generated on most commercial MRI scanners using standard software.

Permeability Maps

From the dynamic contrast enhanced sequence a permeability map ($k_{trans}$) is generated using a modified Brix pharmacokinetic model.

$$S(t) = Dk_{trans}\left[\frac{e^{-k_{trans}t} - e^{-k_{vasc}t}}{k_{vasc} - k_{trans}}\right]$$

S relative signal intensity change from baseline
t time (min)
D scaling constant
$k_{trans}$ permeability constant (min$^{-1}$)
$k_{vasc}$ vascular decay constant (min$^{-1}$)

Scoring

Each map may be scored as follows in a given region, by way of non-limiting values as shown is Scholastic Table Set I:

T2 Weighted Images
0—no cancer
1—dark mass like region 1-4 mm
2—dark mass like region>5 mm
3—dark mass like region with high contrast from adjacent areas>5 mm ADC Maps
0—ADC>1000 mm$^2$/s*10$^{-6}$
3—focal region of ADC<=1000 mm$^2$/s*10$^{-6}$<=3 mm in size
6—focal region of ADC<=1000 mm$^2$/s*10$^{-6}$>3 mm in size Permeability Maps
0—$k_{trans}$<1 min$^{-1}$
1—$k_{trans}$>=1 and <10 min$^{-1}$
2—$k_{trans}$>=10

Figure 1:
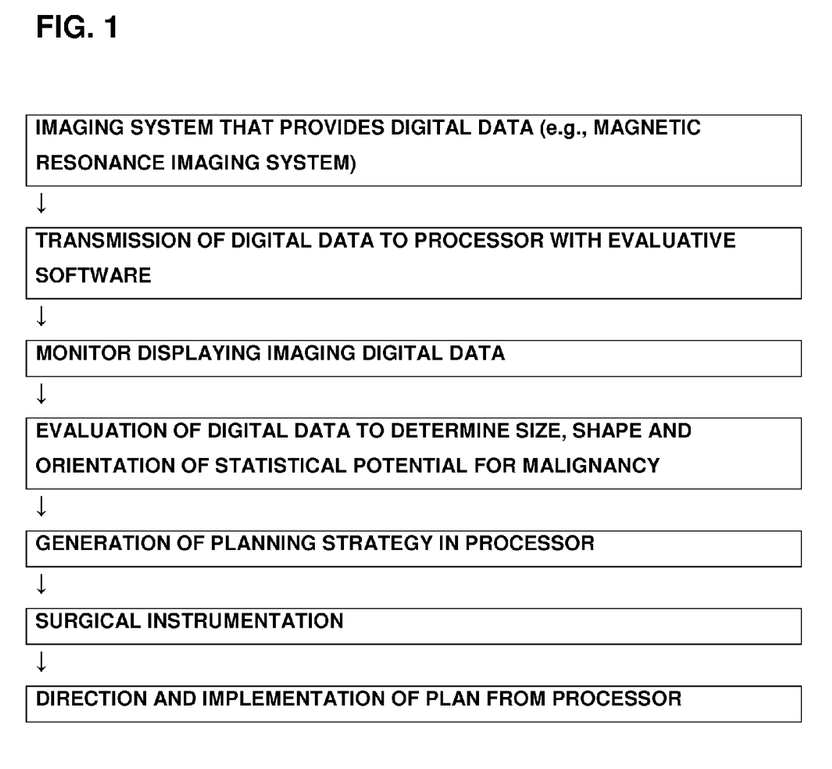
FIG. 1 shows a non-limiting example of a system for performing methods and treatments according to the present invention.

These scores are then summed for the transition zone and peripheral zone and then interpreted as follows:

Total Score for Peripheral Zone
0 no cancer
1-3 possible cancer
4-5 probable cancer
>5 definite cancer Total Score for Transition Zone
<8 no cancer
8-9 possible cancer
10 definite cancer FIG. 1 Axial Pathologic Section and Corresponding MRI Images Showing Tumor
A) Reconstructed pathologic section using older pathologic section method with Gleason 8 tumor outlined by pathologist
B) Corresponding area is outline on T2 weighted image (score 2)
C) ADC map (scale mm$^2$/s*10$^{-6}$) from b-value 600 s/mm$^2$ DWI showing dark cancer region (score 6) ADC while permeability and T2 images show mixed changes
D) Permeability map from a modified Brix model showing cancer region (white region is >20, Score 2)

Total Score is 9=Definite Cancer in the Left Peripheral Zone

Other imaging techniques, including but not limited to MR spectroscopy, ultrasound (with or without a contrast-enhancing agent such as microbubbles) or computer-assisted x-ray imaging, may be used as an alternative to or in combination with MR imaging techniques such as that described above or modifications thereof.

Identification of each focal tumor region may be apparent to a person skilled in the art. Optionally, use of computer software for defining the target volume for local therapy in respect of each image is provided to define the size, shape and location of the 3D target region to be treated. Depending on the treatment modality, an algorithm may then be applied to determine the optimal arrangement of, for example, optical fibers, microwave antenna, ultrasound sources such that the focal target (defined in 3D) is destroyed with minimal damage to the normal, non-cancerous regions of the prostate.

The location of the tumor volume(s) within the prostate are translated into a series of Cartesian coordinates relative to bony landmarks of the pelvis and predetermined surface contours of the prostate.

In the case of energy sources for treatment, a treatment planning algorithm and computer program defines, for each source, the dimensions of the source, its location and orientation within or around the target region and the energy or power to be delivered to the target region. The inputs to this algorithm and program include the location of the target malignant tissues as determined by the MR or other imaging device, information on the method of energy delivery and information on the tissue characteristics that determine the distribution of ablative energy or power in the target and non-target tissues in the prostate. These characteristics may be measured in the individual patient prostate or may be, for example, average characteristics measured in other patients.

This treatment plan may then be formulated to define co-ordinates for manual or robotic-assisted surgery for the ablative energy devices.

In the case of surgical devices, the location of the malignant tissues may be formulated to define co-ordinates for manual or robotic placement and operation of the surgical devices.

An ablative device, operable according to the optimal parameters as determined by the treatment planning algorithm is provided for treatment delivery. In use, the ablative device is guided for delivery of treatment during the therapeutic procedure. This may be in real time. This may be achieved by using other devices to measure, for example, the energy delivery within and surrounding the focal target region of the prostate in order to adjust the treatment plan to account for variations in the properties of the tissue that affect the distribution of the energy. Alternatively, imaging (dynamic or multiple static images) may be used to monitor the changes to the target tissue (including removal of tissue, coagulation, photoactivation, etc) in response to the treatment. One example is the use of MR imaging on-line in order to map the tissue temperature distribution in the case of thermal destruction or to map changes in tissue vascularity or blood flow. Thereby, a feedback process is implemented. This may either open-loop, in which the operator determines the required changes to the procedure, or closed-loop in which these changes are implemented automatically, for example, under computer control.

In the case or robotic or robotic-assisted treatments, the target coordinates formulated from the output of the treatment planning algorithm and program or formulated directly from the location of the malignant tissue determined by the imaging are translated into directives for the imaging-compatible robot. Thus, for example, this places one or more cannulas into the focal tumor according to the selected treatment plan. The energy-delivery device is then placed in the catheter. Alternatively, the delivery device may be inserted directly without a cannula. Image guidance may be used to assist in the placement of the cannulas or delivery devices and/or to check that these are in the correct position before treatment starts. For surgery-based treatment, the robot or robot-assist provides information on the location of the target tissue to be resected. This may involve the use of strereotactic surgical devices.

This multi-step procedure, comprising targeted, controlled and monitored focal tissue destruction, is continued until the target tumor mass of malignant tissue is eliminated with sparing of the remainder of the prostate gland and of predetermined adjacent normal (non-malignant) tissues.

Since various modifications can be made in any invention as herein above described, and many apparently widely different embodiments may be made within the spirit and scope of the claims without departing from the spirit and scope, it is intended that all matter contained in the accompanying specification shall be interpreted as illustrative only and not in a limiting sense.

Working Example on Patient

Mr. CP was a 63-year old man who was diagnosed with prostate cancer on the basis of an elevated PSA (prostate specific antibodies). His clinical stage was T1C and his biopsy showed one core of 6 positive for 15% Gleason grade 6/10 adenocarcinoma. This tumor was in the mid zone of the lateral aspect of the right peripheral portion of the prostate. He sought curative therapy but was discouraged by the known complications of both radical prostatectomy or radiation therapy (both external beam and brachytherapy). He underwent a magnetic resonance scan of the prostate using multimodal MR scanning (MR map). This was a combination of dynamic contrast enhanced MRI (DCEMRI), and apparent diffusion coefficient images (ADC) generated from diffusion weighted imaging and T2 weighted (T2w) MRI. The scoring scheme described earlier (Scholastic Table Set I) was used to identify a cancer at the right base of the prostate in the peripheral zone. This was traced to generate a 3 dimensional map of the tumor location within the prostate that was stored in memory and displayed on a monitor for professional confirmation. This confirmed the location of the cancer and failed to reveal any other suspicious areas. An energy deposition plan was developed using parameters of tissue density (more dense tissue requiring greater energy levels to ablate), energy levels available from the ablative device, direction of energy delivery by device, available positions or orientations of the ablative device during delivery, location of especially sensitive organs or tissue near regions where ablation is to be performed, format of procedure (conservative, versus, moderate, versus aggressive), and the like, to determine a specific ablation procedure delivery plan. This plan would include considerations of time constraints, available entry positions for the ablative device, available orientations of the ablative device delivery tip with respect to different regions of the tumor, and other physical, mechanical and energy parameters so that even a robotic operation with minimal human control over delivery (except as a fail-safe back-up or refining backup). He underwent a confirmatory repeat 14-core prostate biopsy which demonstrated no cancer in any other sector of the prostate. Mr. CP consented to magnetic resonance scan directed, ultrasound guided laser focal ablation of the prostate cancer according to procedures and technology described in the present Patent document. A 3-dimensional map of the location of the cancer within the prostate was constructed from the MR map and a plan for the trajectory for placing the ablative photothermal source (830 nm laser) and power setting of the laser were developed using scholastic analysis of the data and assigning scholastic values based solely on mechanically readable Optical Density measurements in the image such that only the sector containing the cancer would be identified and destroyed (avoiding the urethra, rectum, and neurovascular bundles).

Other methodologies that can be used and might be considered in the determination of a plan might include, but are not limited to, an initial area under the enhancement curve (IAUC) or IAUC normalized to a reference tissue being used as a parameter in the determination of the energy/volume that is to be delivered as a property of location throughout the tumor. This energy per volume may vary depending upon the size and orientation of the tumor (malignant tissue) and the tissue density at the malignant tumor regions and the adjacent benign tissue sites. It is also desirable to use both general curve fitting and model based approaches to DCE MRI analysis as a method of either creating a plan or confirming a plan or confirming tissue evaluations for malignancy versus benignity analysis.

The procedure was performed under general anaesthetic with the patient in the lithotomy position using transrectal ultrasound guidance and a modified brachytherapy template. A translucent needle was advanced through the template into the prostate under ultrasound guidance following the predetermined treatment plan such that the laser lay within the substance of the cancer. The obturator of the needle was removed and the laser fiber was advanced into the sheath of the needle. Thermosensors were advanced into the prostate through the template under ultrasound guidance to the edge of the expected ablation zone (1) and another set placed halfway between this spot and the vital structure (2) (rectum, urethra). The laser was then power up and temperature was monitored until the zone 1 thermosensors reached 55° C. for 5 minutes while the zone 2 thermosensors stayed below 45° C. At that time the hardware was removed and the patient awakened. The patient was discharged home the following day.

A confirmatory gadolinium enhanced magnetic resonance scan 7 days later showed a devascularized zone coincident to the area of the cancer. No side effects (voiding or erectile) were noted by the patient. A biopsy at 3 months showed no evidence of residual cancer in the prostate.

Figure 2:
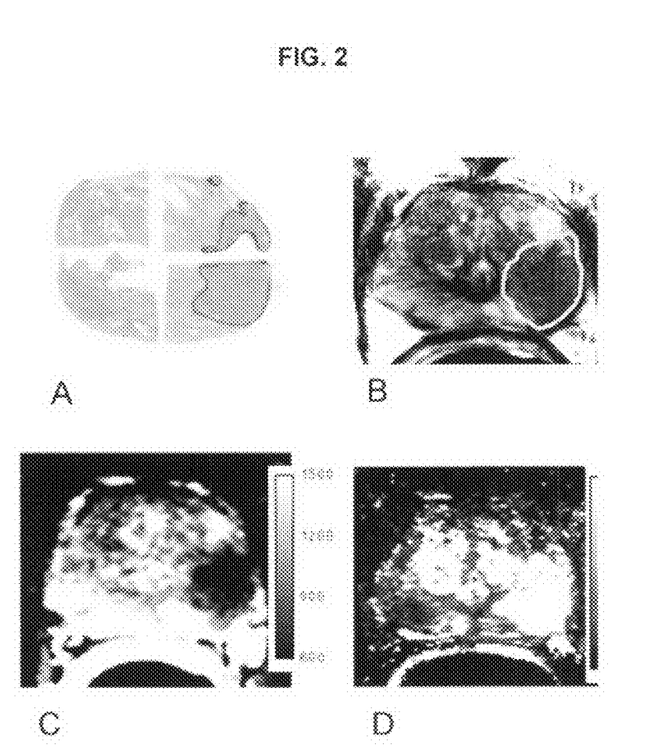
FIG. 2 shows four images indicative of different tissue densities in a prostate.
Figure 3:
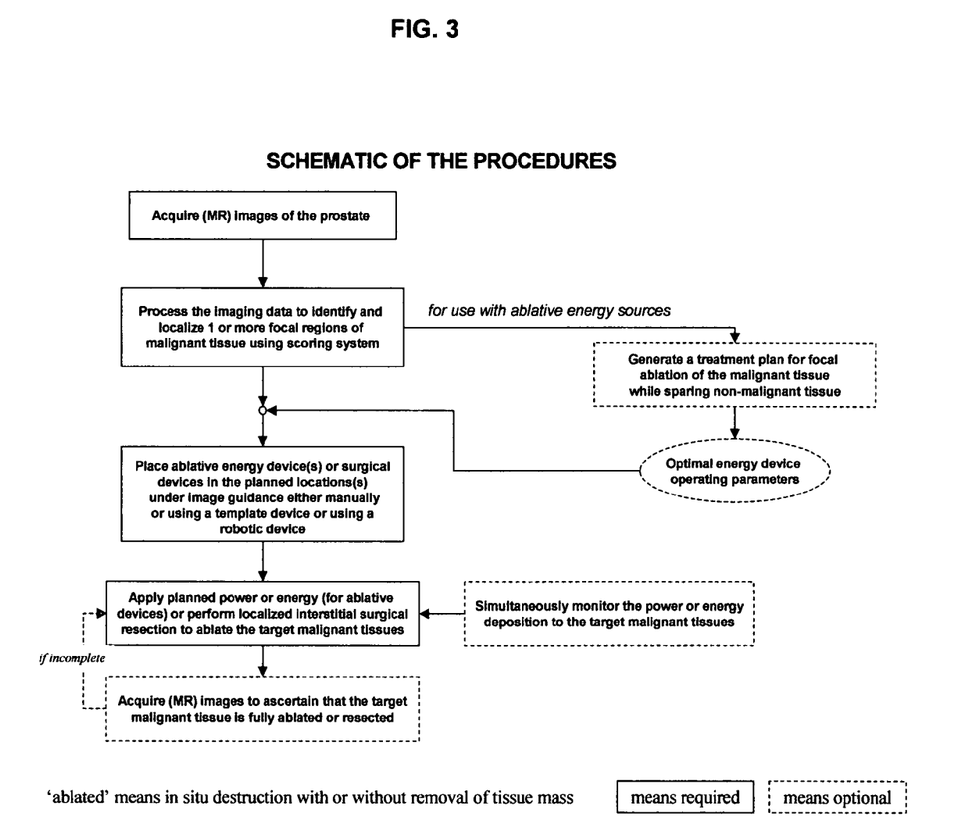
FIG. 3 shows a schematic of a process according to the present technology.

One non-limiting embodiment illustrating the procedures is presented in FIG. 2. The system may be constructed so that the minimally invasive monitoring device is operable for receiving and processing data from a computer hardware and software device. The present invention is defined by the claims appended hereto, with the foregoing description being merely illustrative of a preferred embodiment of the invention. Those of ordinary skill may envisage certain modifications to the foregoing embodiments which, although not explicitly discussed herein, do not depart from the scope of the invention, as defined by the appended claims.

It is also desirable to include-post-imaging techniques such as morphologic based filters and principal component analysis to assist in plan formation. Morphologic filtering and algorithms for applying such filters and rules are taught, by way of non-limiting examples in U.S. Pat. Nos. 5,491,627; 5,588,435; and 6,504,959 (which are incorporated in their entireties herein by reference. Also, it is possible to use known gray-tone morphologic rules directly on the unbinarized image, and one could expand the concept of the pixel "neighborhood" to include non-adjacent pixels, with parameters chosen so as not to thicken "noisy" boundaries too much. These and other graphic analytical techniques can be used to establish scholastic values in determining tumor size, orientation and location from image data taken by non-invasive imaging techniques.

What is claimed:

1. An imaging system in combination with a laser ablation device for differentiating between malignant and non-malignant tissues within the prostate region and for guided delivery of energy from an interstitially positioned laser ablation device acting as tissue removal instrumentation to and within the malignant tissues of the prostate, the imaging and ablation device comprising:
   a) an MRI device for providing real-time, non-invasive imaging data by generating a series of axial MR images through the prostate that differentiates between malignant tissues within the prostate region and for guided delivery of the laser ablation device and guiding delivery of energy;
   b) a processor receiving the generated MR image data and executing a software program on the received generated MR image data to provide an indication of differentiation between malignant and non-malignant tissues of prostate by steps comprising:
      i) inputting variable "a" to represent the presence of malignant tissue and variable "b" to represent the absence of malignant tissue in accordance with T2 weighted, diffusion weighted and dynamic contrast enhanced images further acquired by the MRI device spanning the prostate tissue; and
      ii) using a T1 weighted pulse sequence to obtain at least one additional dynamic contrast enhanced image;
   c) generating an apparent diffusion coefficient map (ADC) on the MRI device;
   d) administering an intravenous contrast agent;
   e) generating a permeability map sing a modified Brix pharmacokinetic model; and
   f) automatically generating a value, by weighting pre-determined regions of the permeability map, to determine the size, location and orientation of the malignant and non-malignant tissue of the prostate represented on an image display;
   g) an energy source for the laser ablation device;
   h) the laser ablation device for interstitial deposition of ablative energy into the malignant prostate tissue being connected to the energy source for the ablation device;
   i) a control system for quantifying the ablation energy interstitially delivered from the laser ablation device into the tissue; and
   the processor is further configured to provide a real-time plan in memory for the energy to be focally delivered interstitially by the laser ablation device to the malignant tissue of the prostate based upon the output information relating to size, location and orientation of the malignant tissue.

2. The system of claim 1 wherein the real-time plan contains variations in laser ablation power and energy applied based upon parameters of tissue density, power and energy levels available from the laser ablation device, direction of energy delivery by the laser ablation device, available positions or orientations of the laser ablation device to provide a trajectory of the laser energy during delivery, and the location of especially sensitive organs or tissue near regions where ablation is to be performed.

3. The system of claim 2 in which a delivery system supplying a pharmaceutical agent is present.

4. The system of claim 2 further comprising a minimally invasive monitoring device for monitoring delivery of the laser energy deposition to a sector about the malignant tissue in real-time.

5. The system of claim 4 wherein the minimally invasive monitoring device also verifies non-destruction of the non-malignant tissue sector in real-time.

6. The system of claim 5 in which the minimally invasive monitoring device comprises a monitor displaying visual information regarding both monitored delivery of the laser energy deposition and verification of non-destruction of the non-malignant tumor tissue in real-time.

7. The system of claim 1 wherein the imagine system is a system providing two distinct imaging capabilities consisting of an MRI device and further comprising at least a second imaging device other than the MRI device.

8. The system of claim 7 wherein the second imaging device is selected from the group consisting of an ultrasound imaging device, x-ray imaging device, and fluoroscopy.

9. The system of claim 1 in which the processor for quantifying energy deposition from the ablative device uses a plan constructed by application of the algorithm to the imaging data in a computer program to provide real-time information of energy deposition to remaining malignant tissue.

10. A method for imaging and ablating malignant tissue from a prostate using resection by non-ablative tools comprising the steps of:
   a) taking real-time, non-invasive MRI imaging data;
   b) executing a software program on the received generated MR image data to provide an indication of differentiation between malignant and non-malignant tissues of prostate by steps comprising:
      i) inputting variable "a" to represent the presence of malignant tissue and variable "b" to represent the absence of malignant tissue in accordance with T2 weighted, diffusion weighted and dynamic contrast enhanced images further acquired by the MRI device spanning the prostate tissue; and
      ii) using a T1 weighted pulse sequence to obtain at least one additional dynamic contrast enhanced image;
   c) generating an apparent diffusion coefficient map (ADC) on the MRI device;
   d) administering an intravenous contrast agent;
   e) generating a permeability map sing a modified Brix pharmacokinetic model; and
   f) automatically generating a value, by weighting pre-determined regions of the permeability map, to determine the size, location and orientation of the malignant and non-malignant tissue of the prostate represented on an image display;

g) providing a laser ablative energy source through or from an interstitially positioned ablation device to interstitially deliver focal ablation energy to the malignant tissue of the prostate in accordance with the determined size, location and orientation of the malignant tissue;

h) operating in real-time a monitoring system quantifying an amount of energy deposited by the laser ablation device; and i) interstitially delivering tissue coagulating or tissue ablating focal therapeutic laser coagulating or laser ablating treatment to the malignant tissue of the prostate, in an amount responsive in real-time to the output data of the monitoring system to deliver laser coagulating or laser ablating energy to only remaining malignant tissue.

11. The method of claim 10 wherein quantifying the amount of energy is representative of physiological changes to be caused by ablation to only remaining malignant tissue.

12. The method of claim 11 wherein determination indicates size, location and orientation of the malignant tissue by application of an algorithm to the imaging data that characterizes in real-time likelihood of grades of data with respect to likelihood of malignancy versus benignity of remaining tissue in a target area.

13. The method of claim 12 wherein the imaging device provides an image display during or after the determination of the size, location and orientation of the malignant tissue and displays the determined size, location and orientation of the malignant tissue.

14. The method of claim 10 wherein the quantified amount of energy generates real-time output data to an ablative device to be used on only remaining malignant tissue.

15. A method for imaging and ablating malignant tissue from a prostate using resection by non-ablative tools comprising the steps of:

a) taking real-time, non-invasive MRI imaging data;

b) executing a software program on the received generated MR image data to provide an indication of differentiation between malignant and non-malignant tissues of prostate by steps comprising:
  i) inputting variable "a" to represent the presence of malignant tissue and variable "b" to represent the absence of malignant tissue in accordance with T2 weighted, diffusion weighted and dynamic contrast enhanced images further acquired by the MRI device spanning the prostate tissue; and
  ii) using a T1 weighted pulse sequence to obtain at least one additional dynamic contrast enhanced image;

c) generating an apparent diffusion coefficient map (ADC) on the MRI device;

d) administering an intravenous contrast agent;

e) generating a permeability map sing a modified Brix pharmacokinetic model; and f) automatically generating a value, by weighting pre-determined regions of the permeability map, to determine the size, location and orientation of the malignant and non-malignant tissue of the prostate represented on an image display;

g) providing a resection medical tool to deliver focal therapy of excision of tissue to the malignant tissue of the prostate in accordance with the determined size, location and orientation of at least the malignant tissue;

h) monitoring in real-time the amount and location of tissue removed and comparing the tissue removing focal therapeutic treatment to determined size, location and orientation of the malignant tissue.

16. The method of claim 15 further comprising operating a monitoring system in real time to display remaining prostate tissue during surgical removal of the malignant tissue to ensure complete removal of the malignant tissue.

\* \* \* \* \*

EX PARTE REEXAMINATION CERTIFICATE (12776th)
United States Patent
Trachtenberg et al.

(10) Number: US 8,548,562 C1
(45) Certificate Issued: Nov. 27, 2024

(54) SYSTEM AND METHOD OF GUIDED TREATMENT WITHIN MALIGNANT PROSTATE TISSUE

(76) Inventors: John Trachtenberg, Toronto (CA); Masoom A. Haider, Richmond Hill (CA); Brian Campbell Wilson, Toronto (CA)

Reexamination Request:
No. 90/019,547, Jun. 20, 2024

Reexamination Certificate for:
Patent No.: 8,548,562
Issued: Oct. 1, 2013
Appl. No.: 11/724,750
Filed: Mar. 16, 2007

Related U.S. Application Data

(60) Provisional application No. 60/788,954, filed on Apr. 4, 2006.

(51) Int. Cl.
*A61B 5/05* (2021.01)
*A61B 18/20* (2006.01)
*A61B 17/00* (2006.01)
*A61B 18/00* (2006.01)
*A61B 90/00* (2016.01)
*A61N 7/02* (2006.01)

(52) U.S. Cl.
CPC .... *A61B 18/20* (2013.01); *A61B 2017/00274* (2013.01); *A61B 2018/00547* (2013.01); *A61B 2018/00636* (2013.01); *A61B 2090/376* (2016.02); *A61B 2090/378* (2016.02); *A61N 7/02* (2013.01)

(58) Field of Classification Search
None
See application file for complete search history.

(56) References Cited

To view the complete listing of prior art documents cited during the proceeding for Reexamination Control Number 90/019,547, please refer to the USPTO's Patent Electronic System.

*Primary Examiner* — Joshua Kading (57) ABSTRACT

An imaging and diagnostic system and method to differentiate between malignant and non-malignant tissue of a prostate and surrounding region. The system acquires imaging data from the prostate and surrounding proximal region, and processes the data to differentiate areas of tissue malignancy from non-malignant tissue. A sectioning device or ablative device is provided. The ablative device is operable by automation for receiving the imaging output coordinates and defining the trajectory and quantity of energy or power to be delivered into the malignant tissue. A control system determines calculated energy or power to be deposited into the malignant tissue during ablation, to minimize destruction of the non-malignant tissue within the prostate and surrounding tissue. The system operates on generated ablative device output data.

EX PARTE REEXAMINATION CERTIFICATE

NO AMENDMENTS HAVE BEEN MADE TO THE PATENT

AS A RESULT OF REEXAMINATION, IT HAS BEEN DETERMINED THAT:

The patentability of claims 1-16 is confirmed.

* * * * *